United States Patent
Ci

(10) Patent No.: US 10,493,119 B2
(45) Date of Patent: Dec. 3, 2019

(54) CHINESE HERBAL ORAL PASTE FOR CONDITIONING BLOOD STASIS CONSTITUTION AND PROCESSING METHOD THEREFOR

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,045

(22) Filed: Apr. 30, 2018

(65) Prior Publication Data

US 2019/0192603 A1    Jun. 27, 2019

(30) Foreign Application Priority Data

Dec. 26, 2017  (CN) .......................... 2017 1 1428988

(51) Int. Cl.

| | |
|---|---|
| *A61K 36/00* | (2006.01) |
| *A61K 36/64* | (2006.01) |
| *A61K 36/232* | (2006.01) |
| *A61K 36/533* | (2006.01) |
| *A61K 36/736* | (2006.01) |
| *A61K 36/28* | (2006.01) |
| *A61K 36/484* | (2006.01) |
| *A61K 36/752* | (2006.01) |
| *A61K 36/346* | (2006.01) |
| *A61K 36/738* | (2006.01) |
| *A61K 35/586* | (2015.01) |
| *A61K 47/26* | (2006.01) |
| *A61K 45/06* | (2006.01) |
| *A61K 9/00* | (2006.01) |
| *A61P 7/00* | (2006.01) |
| *A61K 36/65* | (2006.01) |

(52) U.S. Cl.
CPC ............ *A61K 36/64* (2013.01); *A61K 9/0053* (2013.01); *A61K 35/586* (2013.01); *A61K 36/232* (2013.01); *A61K 36/28* (2013.01); *A61K 36/346* (2013.01); *A61K 36/484* (2013.01); *A61K 36/533* (2013.01); *A61K 36/65* (2013.01); *A61K 36/736* (2013.01); *A61K 36/738* (2013.01); *A61K 36/752* (2013.01); *A61K 45/06* (2013.01); *A61K 47/26* (2013.01); *A61P 7/00* (2018.01); *A61K 2236/13* (2013.01); *A61K 2236/51* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue

(57) ABSTRACT

The present application discloses a Chinese herbal oral paste for conditioning blood stasis constitution. The Chinese herbal oral paste includes the following components: unprocessed rehmannia root, peony root, angelica, sichuan lovage rhizome, motherwort herb, peach seed, safflower, licorice, orange fruit, platycodon root, twotoothed achyranthes root, rose flower, cortex moutan, kudzu vine root, nutgrass galingale rhizome, unprocessed cattail pollen, Chinese cinnamon, earthworm, suberect spatholobus stem, largeleaf gentian root, milkvetch root, snakegourd root, danshen root, sanqi powder, India madder root, unprocessed hawthorn fruit, donkey-hide gelatin, turtle shell gelatin, tortoise-plastron gelatin, xylitol, and stir-baked squama manitis. The Chinese herbal oral paste of the present disclosure has a higher drug concentration and good taste, is particularly suitable for health preserving in winter and conditioning the blood stasis constitution, will not create negative effects or harm to the human body at all, and is capable of achieving certain efficacy of strengthening physical health.

20 Claims, 1 Drawing Sheet

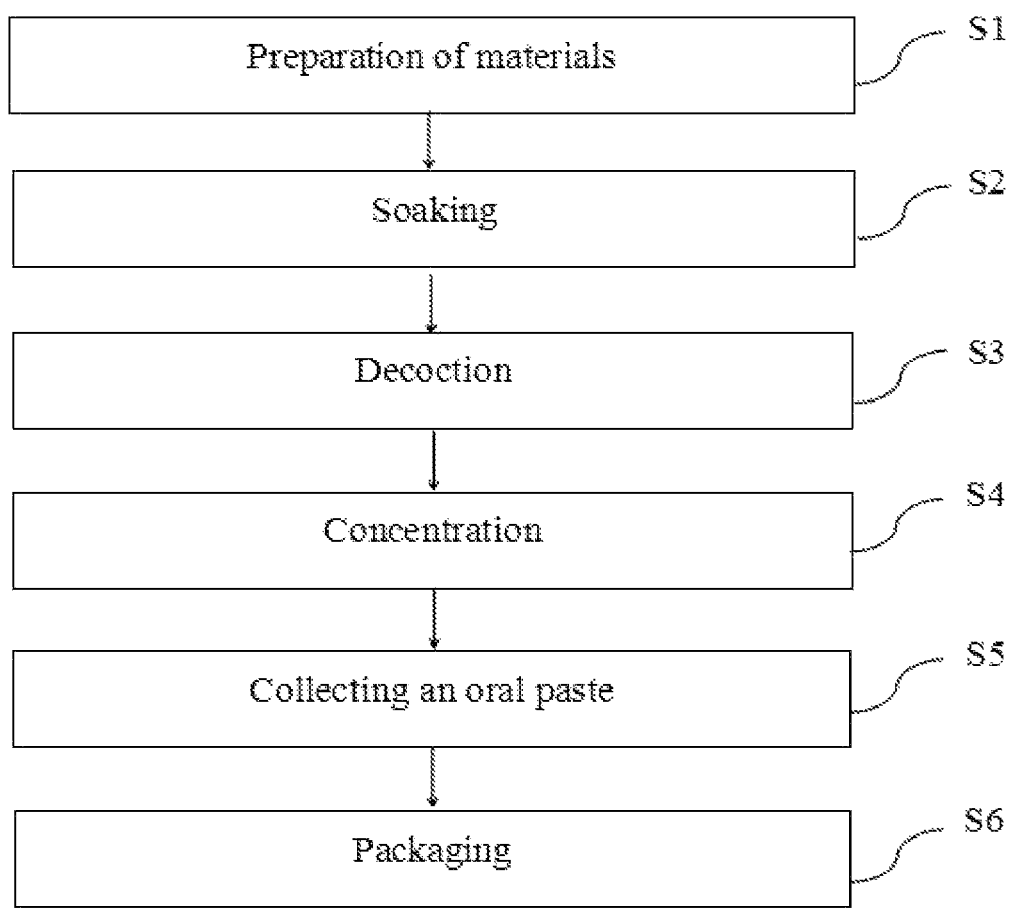

CHINESE HERBAL ORAL PASTE FOR CONDITIONING BLOOD STASIS CONSTITUTION AND PROCESSING METHOD THEREFOR

TECHNICAL FIELD

The present disclosure relates to the field of health foods, and particularly to a Chinese herbal oral paste for conditioning blood stasis constitution and a processing method therefor.

BACKGROUND

In *Classification and Determination of Constitution in Traditional Chinese Medicine*, the China Association of Chinese Medicine classifies constitutions of the human body into nine types, including yin-yang harmony constitution, yang deficiency constitution, yin deficiency constitution, qi deficiency constitution, phlegm-dampness constitution, damp-heat constitution, qi depression constitution, blood stasis constitution, and allergic constitution, most of which belong to sub-healthy states.

The main symptom of blood stasis constitution is sluggish circulation of the blood, which is mainly caused by dysfunction of internal organs due to prolonged depression of emotion and volition or long-term residence in cold places, and mainly occurs in relatively thin people. The clinical manifestation is as follows: when blood stagnates at a certain place of the internal organs or of main and collateral channels, a pain is incurred at a fixed place, and the pain cannot be relieved with warmness, and even leads to the formation of a lump. For people with such constitution, some have senile plaques even when they are not old enough, and some often suffer from a pain in a certain place of the body. For example, the female easily have dysmenorrhea in the menstrual period; the male usually have bruises on their bodies, and the pain in the body worsens at night, etc.

Such sub-healthy constitution as blood stasis constitution belongs to chronic diseases and has a relatively long disease course, and requires a long-term medication and gradual conditioning, in order to achieve the effects of consolidating the vital essence and strengthening the origin, and strengthening the body resistance to eliminate pathogenic factors. The drug forms commonly used in the traditional Chinese medicine are decoctions and Chinese patent medicine such as pills and the like. Decoctions usually have relatively good efficacy, but the administration thereof is complicated, and the taste thereof is poor. If the decoctions need to be prepared for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and susceptibility to diseases. It is believed in the traditional Chinese medicine that since the human beings live in the natural world, physiological functions of the human body usually change with seasons, that is, "correspondence between man and nature". Winter is the season when the human body "stores energies", thus appropriate nourishment can enhance the constitution, ward off diseases and strengthen the body, and prolong life, that is, conditioning in winter or nourishing in winter commonly mentioned in the traditional Chinese medicine. For the sub-healthy population with blood stasis constitution, a solid oral paste with a higher drug concentration and good taste, and being convenient to carry more meets requirements of modern people.

SUMMARY

A main object of the present disclosure is to provide a Chinese herbal nourishing product suitable for conditioning in winter so as to treat blood stasis constitution.

In order to achieve the above object, according to one aspect of the present disclosure, there is provided a Chinese herbal oral paste for conditioning blood stasis constitution.

The Chinese herbal oral paste for conditioning blood stasis constitution according to the present disclosure includes the following components in parts by weight: 5-19 parts of unprocessed rehmannia root, 6-17 parts of peony root, 6-15 parts of angelica, 3-14 parts of sichuan lovage rhizome, 7-18 parts of motherwort herb, 6-15 parts of peach seed, 2-10 parts of safflower, 1-5 parts of licorice, 6-15 parts of orange fruit, 4-13 parts of platycodon root, 4-13 parts of twotoothed achyranthes root, 5-17 parts of rose flower, 3-14 parts of cortex moutan, 10-27 parts of kudzu vine root, 3-9 parts of nutgrass galingale rhizome, 5-16 parts of unprocessed cattail pollen, 1-5 parts of Chinese cinnamon, 6-17 parts of earthworm, 13-30 parts of suberect spatholobus stem, 6-14 parts of largeleaf gentian root, 8-17 parts of milkvetch root, 8-17 parts of snakegourd root, 7-17 parts of danshen root, 6-16 parts of sanqi powder, 7-16 parts of India madder root, 12-31 parts of unprocessed hawthorn fruit, 5-15 parts of donkey-hide gelatin, 10-22 parts of turtle shell gelatin, 9-21 parts of tortoise-plastron gelatin, 20-40 parts of xylitol, and 3-9 parts of stir-baked squama manitis.

Furthermore, the Chinese herbal oral paste for conditioning blood stasis constitution according to the present disclosure includes the following components in parts by weight: 8-16 parts by weight of unprocessed rehmannia root, 9-15 parts by weight of peony root, 8-12 parts by weight of angelica, 5-11 parts by weight of sichuan lovage rhizome, 9-15 parts by weight of motherwort herb, 8-12 parts by weight of peach seed, 4-8 parts by weight of safflower, 2-4 parts by weight of licorice, 8-12 parts by weight of orange fruit, 6-10 parts by weight of platycodon root, 6-10 parts by weight of twotoothed achyranthes root, 9-14 parts by weight of rose flower, 6-10 parts by weight of cortex moutan, 15-25 parts by weight of kudzu vine root, 5-7 parts by weight of nutgrass galingale rhizome, 8-13 parts by weight of unprocessed cattail pollen, 1-3 parts by weight of Chinese cinnamon, 9-13 parts by weight of earthworm, 15-25 parts by weight of suberect spatholobus stem, 8-12 parts by weight of largeleaf gentian root, 10-14 parts by weight of milkvetch root, 10-14 parts by weight of snakegourd root, 10-15 parts by weight of danshen root, 8-13 parts by weight of sanqi powder, 9-14 parts by weight of India madder root, 15-25 parts by weight of unprocessed hawthorn fruit, 8-13 parts by weight of donkey-hide gelatin, 12-18 parts by weight of turtle shell gelatin, 12-18 parts by weight of tortoise-plastron gelatin, 25-35 parts by weight of xylitol, and 5-7 parts by weight of stir-baked squama manitis.

Furthermore, the Chinese herbal oral paste for conditioning blood stasis constitution according to the present disclosure includes the following components in parts by weight: 12 parts by weight of unprocessed rehmannia root, 12 parts by weight of peony root, 10 parts by weight of angelica, 8 parts by weight of sichuan lovage rhizome, 12 parts by weight of motherwort herb, 10 parts by weight of peach seed, 6 parts by weight of safflower, 3 parts by weight of licorice, 10 parts by weight of orange fruit, 8 parts by weight of platycodon root, 8 parts by weight of twotoothed achyranthes root, 12 parts by weight of rose flower, 8 parts by weight of cortex moutan, 20 parts by weight of kudzu vine root, 6 parts by weight of nutgrass galingale rhizome, 10 parts by weight of unprocessed cattail pollen, 2 parts by weight of Chinese cinnamon, 10 parts by weight of earthworm, 20 parts by weight of suberect spatholobus stem, 10 parts by weight of largeleaf gentian root, 12 parts by weight of milkvetch root, 12 parts by weight of snakegourd root, 12 parts by weight of danshen root, 10 parts by weight of sanqi powder, 12 parts by weight of India madder root, 20 parts by weight of unprocessed hawthorn fruit, 10 parts by weight of donkey-hide gelatin, 15 parts by weight of turtle shell gelatin, 15 parts by weight of tortoise-plastron gelatin, 30 parts by weight of xylitol, and 6 parts by weight of stir-baked squama manitis.

In order to achieve the above object, according to the other aspect of the present disclosure, there is a processing method for a Chinese herbal oral paste for conditioning blood stasis constitution.

The processing method for a Chinese herbal oral paste for conditioning blood stasis constitution according to the present disclosure includes the following steps in sequence: preparation of materials, soaking, decoction, concentration, and collecting an oral paste.

Furthermore, the step of preparation of materials is: measuring raw materials of formula ratio according to composition of the Chinese herbal oral paste, and washing raw materials, except tortoise-plastron gelatin, turtle shell gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by stirring while decocting and concentrating with low heat, until the drug liquid does not disperse when being dropped on paper, to obtain a vegetarian paste.

Furthermore, the step of collecting an oral paste is: pouring xylitol, and melted tortoise-plastron gelatin, turtle shell gelatin, and donkey-hide gelatin into the vegetarian paste respectively, stirring them continuously with a shovel while cooking them slowly with low heat, until the juice coagulates into beads when dropped into clear water and does not disperse, and canning the resulted oral paste.

The melting step is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

The Chinese herbal oral paste of the present disclosure has a higher drug concentration and good taste, is particularly suitable for health preserving in winter and conditioning the blood stasis constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

A Chinese herbal oral paste for conditioning blood stasis constitution of the present disclosure includes the following components: unprocessed rehmannia root, peony root, angelica, sichuan lovage rhizome, motherwort herb, peach seed, safflower, licorice, orange fruit, platycodon root, twotoothed achyranthes root, rose flower, cortex moutan, kudzu vine root, nutgrass galingale rhizome, unprocessed cattail pollen, Chinese cinnamon, earthworm, suberect spatholobus stem, largeleaf gentian root, milkvetch root, snakegourd root, danshen root, sanqi powder, India madder root, unprocessed hawthorn fruit, donkey-hide gelatin, turtle shell gelatin, tortoise-plastron gelatin, xylitol, and stir-baked squama manitis.

Unprocessed rehmannia root is sweet and cold, acts on heart, liver, and kidney, removes heat and cools blood, nourishes yin, promotes the secretion of body fluid, and is used for fever crimson tongue and polydipsia, yin-deficiency internal heat, steaming bone consumptive fever, internal-heat consumptive thirst, hematemesis, bleeding from five sense organs or subcutaneous tissue, and eruption and rash.

Peony root is bitter in flavor and slightly cold in nature, acts on liver, removes heat and cools blood, removes blood stasis to stop pain, and is used for nutritive blood due to heat invasion, warm toxin eruption, hematemesis and bleeding from five sense organs or subcutaneous tissue, sore red swollen eyes, liver depression and hypochondriac pain, amenorrhea and dysmenorrhea, abdominal mass pain, traumatic injury, and ulcer and skin and external diseases.

Angelica is sweet, acrid, and warm, acts on liver, heart, and spleen, replenishes blood, invigorates the circulation of blood, regulates menstruation and stops pain, moistens dryness and lubricates intestines, and is mainly used for various blood-deficiency symptoms, irregular menstruation, amenorrhea, dysmenorrhea, abdominal mass agglomeration, metrorrhagia and metrostaxis, deficiency-cold stomachache, paralysis, numbness of skin, intestinal dryness and difficult defecation, dysentery tenesmus, ulcer and skin and external diseases, and traumatic injury.

Sichuan lovage rhizome is acrid and warm, acts on liver and gallbladder, promotes the circulation of qi and resolves depression, dispels wind and dries dampness, invigorates blood circulation to stop pain, treats wind-coldness headache and vertigo, hypochondriac pain and stomachache, arthritis and cramps, amenorrhea, dystocia, postpartum obstruction and pain, ulcer and skin and external diseases, and is used for irregular menstruation, amenorrhea and dysmenorrhea, abdominal mass pain, prickling in chest and hypochondrium, traumatic gall, headache, and arthralgia due to wind-dampness.

Motherwort herb is bitter, acrid and slightly cold, acts on liver, pericardium, and bladder, invigorates the circulation of blood and regulates menstruation, promotes urination and relieves swelling, removes heat and toxic matters, and is used for irregular menstruation, dysmenorrhea and amenorrhea, endless lochia, edema and oliguria, and toxic swelling of skin and external diseases.

Peach seed is bitter, sweet and neutral, acts on heart, liver and large intestine, invigorates blood circulation to remove blood stasis, lubricates intestine to relax bowel, and relieves cough and asthma, and is used for amenorrhea and dysmenorrhea, lump in the abdomen, pulmonary abscess and intestinal carbuncle, traumatic injury, constipation due to intestinal dryness, and cough and dyspnea.

Safflower is acrid and warm, acts on heart and liver, invigorates the circulation of blood and menstruation, removes stasis to stop pain, and treats amenorrhea, abdominal mass, dystocia, fetal death, postpartum lochia, pain due to blood stasis, abscess, and traumatic injury.

Licorice is sweet and neutral, acts on heart, lung, spleen, and stomach, supplements spleen and tonifies qi, removes heat and toxic matters, eliminates phlegm and relieves cough, relieves spasm and alleviates pain, moderates various drugs, and is used for weakness of spleen and stomach, lassitude and asthenia, palpitation and short of breath, cough with excessive phlegm, abdominal distention, four-limb spasm and pain, carbuncle, and alleviation of drug toxicity and intensity.

Orange fruit is bitter, acrid, sour, and slightly cold, acts on spleen and stomach, regulates qi and the middle energizer, removes stagnation and flatulence, and is used for distending pain in chest and qi stagnation, distention and pain, indigestion, phlegm-fluid retention and congestion, and splanchnoptosis.

Platycodon root is bitter and acrid in flavor and neutral in natures, acts on lung, facilitates the flow of the lung-qi, relieves sore throat, eliminates phlegm, expels pus, and is used for cough with copious whitish viscid sputum, oppression in the chest, pharyngalgia and hoarseness, pulmonary abscess and pyemesis.

Twotoothed achyranthes root is bitter, sweet, sour, and neutral, acts on liver and kidney, eliminates stasis and restores menstrual flow, nourishes liver and kidney, strengthens muscles and bones, induces diuresis for treating stranguria, ensures proper downward flow of the blood, and is used for amenorrhea, dysmenorrhea, waist and knee pain, weakness in muscles and bones, stranguria, edema, headache, vertigo, toothache, bedsore, hematemesis, and bleeding from five sense organs or subcutaneous tissue.

Rose flower is sweet and slight bitter in flavor and warm in nature, acts on liver, spleen, and stomach, promotes qi and blood circulation, treats wind arthralgia, dispels fatigue and stops pain, and is used for hypermenorrhea, leukorrhea with reddish discharge and enteritis, bowel complaint, intestinal haemorrhage, etc.

Cortex moutan is bitter and acrid in flavor and slightly cold in nature, acts on heart, liver, and stomach, removes heat to cool blood, invigorates blood circulation to remove blood stasis, eliminates deficient heat, and is used for blood-heat haematemesis, eruption, yin-deficiency internal heat, anhidrotic steaming bone, amenorrhea and algomenorrhea, traumatic injury, swelling pain of skin and external diseases, and intestinal carbuncle and stomachache.

Kudzu vine root is sweet and acrid in flavor and cool in nature, acts on lung and stomach, relieves the muscles and skin and allay fever, promotes eruption, promotes the secretion of body fluid and quenches thirst, invigorates yang and cures diarrhea, and is used for treatment of syndrome of fever, sever back pain, measles without adequate eruption, thirst caused by fever, yin-deficiency diabetes, heat diarrhea, and spleen-deficiency diarrhea.

Nutgrass galingale rhizome is acrid, slightly bitter, slightly sweet, and neutral, acts on liver, spleen, and triple energizer meridian, soothes liver and resolves depression, egulates qi and the middle energizer, regulates menstruation and relieves pain, and is used for liver depression and qi stagnation, distending pain in chest and hypochondrium, hernia pain, breast tenderness, qi stagnation of spleen and stomach, abdominal fullness and stuffy feeling in chest, distention and fullness pain, irregular menstruation, and amenorrhea and algomenorrhea.

Unprocessed cattail pollen is sweet and neutral, acts on liver and pericardium meridian, stops bleeding, dissolves stasis, treats stranguria, and is used for hematemesis, bleeding from five sense organs or subcutaneous tissue, hemoptysis, metrorrhagia and metrostaxis, traumatic bleeding, amenorrhea and dysmenorrhea, prickling in chest and stomach, traumatic gall, and painful and diffecult hematuria.

Chinese cinnamon is hot in nature, acrid and sweet in flavor, acts on kidney, spleen, heart, and liver, tonifies fire and helps yang, eliminates cold to stop pain, warms and unblocks meridians, and is used for kidney-yang insufficiency, impotence and uterine cold, abdominal cold and pain, arthritis and waist pain, cold abdominal colic stomachache, blood stasis due to cold accumulation, amenorrhea and dysmenorrhea, and chest obstruction and cardiac pain.

Earthworm is salty and cold, acts on liver, spleen, and bladder, removes heat to calm endogenous wind, clearing and activating channels and collaterals, clears lung and relieves asthma, removes heat to induce urination, and is used for high fever epilepsy, dementedness, arthralgia and paralysis of half body, lung heat asthma, heat accumulation of bladder, difficult urination or anuresis.

Suberect spatholobus stem is bitter, sweet, and warm, acts on liver and kidney, invigorates the circulation of blood and replenishes blood, regulates menstruation and relieves pain, relaxes tendons and activates collaterals, and is used for irregular menstruation, algomenorrhea, amenorrhea, rheumatic arthralgia, numbness paralysis, and blood deficiency and etiolation.

Largeleaf gentian root is acrid and bitter in flavor and neutral in nature, acts on stomach, liver, and gallbladder, has the efficacies of dispelling wind-dampness, removing dampness heat, relieving arthralgia, and removing deficiency heat, and is used for rheumatic arthralgia, paralysis of half body due to stroke, spasm in muscle and vessel, soreness and weakness of joints, jaundice due to damp-heat, and hectic fever due to yin-deficiency and infantile malnutrition fever.

Milkvetch root is sweet and slightly warm, acts on lung, spleen, liver, and kidney, is mostly used for spontaneous perspiration due to weakness, deficiency edema due to insufficiency of yang qi, chronic nephritic edema, spleen and kidney deficiency, invagination of skin and external diseases due to long-term non-bursting, bursting of skin and external diseases, lasting cough and asthma, shortness of breath and mental weariness, phlegm present in lung which cannot be coughed out, lassitude, or sinking of qi of middle energizer, rectocele, and uterine prolapse.

Snakegourd root is sweet and slight bitter and slightly cold, acts on lung and stomach, removes heat and purges pathogenic fire, promotes the secretion of body fluid and allays thirst, diminishes swelling and expels pus, and is used for pyreticosis polydipsia, cough due to the lung heat, internal-heat consumptive thirst, sore, ulcer and pyogenic infections.

Danshen root is bitter in flavor and slightly cold, acts on heart and liver, invigorates blood circulation to remove blood stasis, induces menstruation to stop pain, clears away the heart fire and relieves restlessness, cools blood to resolve carbuncle, and is used for chest stuffiness and pains, abdominal fullness and hypochondriac pain, mass accumulation in abdomen, heat arthralgia pain, dysphoria insomnia, irregular menstruation, dysmenorrhea and amenorrhea, and swelling pain of skin and external diseases.

Sanqi powder is bitter in flavor with sweetness, and warm in nature, acts on liver and stomach, stops bleeding, invigorates blood circulation to remove stasis, diminishes swelling and settles pain, nourishes and strengthens body, resists fatigue, hypoxia, and aging, lowers blood lipid and blood pressure, improves immune function of organism, etc., treats various internal and external bleeding syndromes such as traumatic bleeding, blood stasis, gastric bleeding, and urine blood, expands vessel, dissolves blood clots, improves microcirculation, prevents and treats cardiovascular and cerebrovascular diseases such as high blood fat, high cholesterol, coronary heart disease, angina pectoris, cerebral hemorrhage sequel, liver diseases such as fatty liver and hepatic fibrosis, and weakness syndromes caused by blood loss, long illness and after childbirth, etc.

India madder root is bitter and cold, acts on liver, cools blood to stop bleeding, invigorates blood circulation to dispel stasis, cools blood to promote the circulation of blood, removes stasis, restores menstrual flow, and is used for hematemesis, bleeding from five sense organs or subcutaneous tissue, metrorrhagia and metrostaxis, traumatic bleeding, amenorrhea obstruction, joint arthralgia, traumatic gall, cools blood and stops bleeding, promotes the circulation of blood to remove blood stasis, and is used for heat syndrome bleeding, amenorrhea abdominal pain, and traumatic injury.

Unprocessed hawthorn fruit is sour, sweet, and slightly warm, acts on spleen, stomach and liver, promotes digestion, dissipates blood stasis, expels tapeworm, treats meat-type food accumulation, abdominal mass, phlegm retention, distention and fullness, acid regurgitation, diarrhea, intestinal wind, waist pain, hernia, postpartum abdominal pain, endless lochia, infantile stagnation of milk and food, promotes digestion, promotes the circulation of qi and dissipates blood stasis.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

Turtle shell gelatin is sweet and salty in flavor and slightly cold in nature, acts on liver, lung, and kidney, nourishes yin and allays fever, resolves hard lump, and is used for yin-deficiency hectic fever, consumptive disease and hemoptysis, chronic malaria, malaria with abdominal mass, hemorrhoids gall, and blood-deficiency amenorrhea.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea.

Stir-baked squama manitis is salty in flavor and slightly cold in nature, acts on liver and stomach, invigorates the circulation of blood to remove stasis, stimulates the menstrual flow and promotes lactation, resolves carbuncle, and is mainly used for blood stasis menstrual block, abdominal mass, rheumatic arthralgia, breast milk stoppage, abscess, and crewels.

The blood stasis constitution refers to the body constitution prone to sluggish circulation of the blood or incapability of dissipation of internal hemorrhage to cause internal stagnation of the blood, when internal organs are dysfunctional, which often has the manifestations of dark complexion, rough and brown skin, chromatosis possibly with purpura, pale lips, cyanotic tongue possibly with petechiae, and thready and uneven pulse. The blood stasis constitution has varied symptoms, and the general therapeutic principle is invigorating blood circulation to dispel stasis. The Chinese herbal oral paste of the present disclosure can directly expand vessels to reduce peripheral resistance, invigorate the blood circulation to dispel stasis, and treats various syndromes of pain of the blood stasis constitution. With the multiple types of drug materials of large dosages, efficacies of the various drug materials generate a synergistic effect, with the functions of promoting the circulation of blood and nourishing blood, and the blood stasis constitution can be corrected, so that people are vigorous with strong resistibility, and the occurrence of diseases is avoided. With the correction for such constitution, it is more targeted and will not create side effects, without harm to the human body at all, and can achieve certain efficacy of strengthening the body.

As shown in FIG. 1, the processing method for the Chinese herbal oral paste for conditioning blood stasis constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1

A Chinese herbal oral paste for conditioning blood stasis constitution includes the following components in parts by weight: 5 parts of unprocessed rehmannia root, 6 parts of peony root, 6 parts of angelica, 3 parts of sichuan lovage rhizome, 7 parts of motherwort herb, 6 parts of peach seed, 2 parts of safflower, 1 parts of licorice, 6 parts of orange fruit, 4 parts of platycodon root, 4 parts of twotoothed achyranthes root, 5 parts of rose flower, 3 parts of cortex moutan, 10 parts of kudzu vine root, 3 parts of nutgrass galingale rhizome, 5 parts of unprocessed cattail pollen, 1 parts of Chinese cinnamon, 6 parts of earthworm, 13 parts of suberect spatholobus stem, 6 parts of largeleaf gentian root, 8 parts of milkvetch root, 8 parts of snakegourd root, 7 parts of danshen root, 6 parts of sanqi powder, 7 parts of India madder root, 12 parts of unprocessed hawthorn fruit, 5 parts of donkey-hide gelatin, 10 parts of turtle shell gelatin, 9 parts of tortoise-plastron gelatin, 20 parts of xylitol, and 3 parts of stir-baked squama manitis.

The processing method therefor includes the following steps in sequence:

preparation of materials: measuring raw materials of formula ratio according to composition of the Chinese herbal oral paste, and washing raw materials, except tortoise-plastron gelatin, turtle shell gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering drug juice with gauze, then soaking filtered dregs of decoction with clear water and decocting the soaked dregs of decoction with low heat for 1 hour, thus repeating 4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted tortoise-plastron gelatin, turtle shell gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 2

A Chinese herbal oral paste for conditioning blood stasis constitution includes the following components in parts by weight: 19 parts of unprocessed rehmannia root, 17 parts of peony root, 15 parts of angelica, 14 parts of sichuan lovage rhizome, 18 parts of motherwort herb, 15 parts of peach seed, 10 parts of safflower, 5 parts of licorice, 15 parts of orange fruit, 13 parts of platycodon root, 13 parts of twotoothed achyranthes root, 17 parts of rose flower, 14 parts of cortex moutan, 27 parts of kudzu vine root, 9 parts of nutgrass galingale rhizome, 16 parts of unprocessed cattail pollen, 5 parts of Chinese cinnamon, 17 parts of earthworm, 30 parts of suberect spatholobus stem, 14 parts of largeleaf gentian root, 17 parts of milkvetch root, 17 parts of snakegourd root, 17 parts of danshen root, 16 parts of sanqi powder, 16 parts of India madder root, 31 parts of unprocessed hawthorn fruit, 15 parts of donkey-hide gelatin, 22 parts of turtle shell gelatin, 21 parts of tortoise-plastron gelatin, 40 parts of xylitol, and 9 parts of stir-baked squama manitis.

The processing method therefor includes the following steps in sequence:

preparation of materials: measuring raw materials of formula ratio according to composition of the Chinese herbal oral paste, and washing raw materials, except tortoise-plastron gelatin, turtle shell gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering drug juice with gauze, then soaking filtered dregs of decoction with clear water and decocting the soaked dregs of decoction with low heat for 1 hour, then repeating 2 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted tortoise-plastron gelatin, turtle shell gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 3

A Chinese herbal oral paste for conditioning blood stasis constitution includes the following components in parts by weight: 8 parts of unprocessed rehmannia root, 9 parts of peony root, 8 parts of angelica, 5 parts of sichuan lovage rhizome, 9 parts of motherwort herb, 8 parts of peach seed, 4 parts of safflower, 2 parts of licorice, 8 parts of orange fruit, 6 parts of platycodon root, 6 parts of twotoothed achyranthes root, 9 parts of rose flower, 6 parts of cortex moutan, 15 parts of kudzu vine root, 5 parts of nutgrass galingale rhizome, 8 parts of unprocessed cattail pollen, 1 parts of Chinese cinnamon, 9 parts of earthworm, 15 parts of suberect spatholobus stem, 8 parts of largeleaf gentian root, 10 parts of milkvetch root, 10 parts of snakegourd root, 10 parts of danshen root, 8 parts of sanqi powder, 9 parts of India madder root, 15 parts of unprocessed hawthorn fruit, 8 parts of donkey-hide gelatin, 12 parts of turtle shell gelatin, 12 parts of tortoise-plastron gelatin, 25 parts of xylitol, and 5 parts of stir-baked squama manitis.

The processing method therefor includes the following steps in sequence:

preparation of materials: measuring raw materials of formula ratio according to composition of the Chinese herbal oral paste, and washing raw materials, except tortoise-plastron gelatin, turtle shell gelatin, donkey-hide gelatin, and xylitol, for subsequent use;

soaking: soaking the cleaned raw materials with 9 folds of water for 9 h, with the water over the raw materials by 12 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, and melted tortoise-plastron gelatin, turtle shell gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 4

A Chinese herbal oral paste for conditioning blood stasis constitution includes the following components in parts by weight: 16 parts of unprocessed rehmannia root, 15 parts of peony root, 12 parts of angelica, 11 parts of sichuan lovage rhizome, 15 parts of motherwort herb, 12 parts of peach seed, 8 parts of safflower, 4 parts of licorice, 12 parts of orange fruit, 10 parts of platycodon root, 10 parts of twotoothed achyranthes root, 14 parts of rose flower, 10 parts of cortex moutan, 25 parts of kudzu vine root, 7 parts of nutgrass galingale rhizome, 13 parts of unprocessed cattail pollen, 3 parts of Chinese cinnamon, 13 parts of earthworm, 25 parts of suberect spatholobus stem, 12 parts of largeleaf gentian root, 14 parts of milkvetch root, 14 parts of snakegourd root, 15 parts of danshen root, 13 parts of sanqi powder, 14 parts of India madder root, 25 parts of unprocessed hawthorn fruit, 13 parts of donkey-hide gelatin, 18 parts of turtle shell gelatin, 18 parts of tortoise-plastron gelatin, 35 parts of xylitol, and 7 parts of stir-baked squama manitis.

The processing method therefor includes the following steps in sequence:

preparation of materials: measuring raw materials of formula ratio according to composition of the Chinese herbal oral paste, and washing raw materials, except tortoise-plastron gelatin, turtle shell gelatin, donkey-hide gelatin, and xylitol, for subsequent use;

soaking: soaking the cleaned raw materials with 9 folds of water for 11 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted tortoise-plastron gelatin, turtle shell gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 5

A Chinese herbal oral paste for conditioning blood stasis constitution includes the following components in parts by weight: 12 parts of unprocessed rehmannia root, 12 parts of peony root, 10 parts of angelica, 8 parts of sichuan lovage rhizome, 12 parts of motherwort herb, 10 parts of peach seed, 6 parts of safflower, 3 parts of licorice, 10 parts of orange fruit, 8 parts of platycodon root, 8 parts of twotoothed achyranthes root, 12 parts of rose flower, 8 parts of cortex moutan, 20 parts of kudzu vine root, 6 parts of nutgrass galingale rhizome, 10 parts of unprocessed cattail pollen, 2 parts of Chinese cinnamon, 10 parts of earthworm, 20 parts of suberect spatholobus stem, 10 parts of largeleaf gentian root, 12 parts of milkvetch root, 12 parts of snakegourd root, 12 parts of danshen root, 10 parts of sanqi powder, 12 parts of India madder root, 20 parts of unprocessed hawthorn fruit, 10 parts of donkey-hide gelatin, 15 parts of turtle shell gelatin, 15 parts of tortoise-plastron gelatin, 30 parts of xylitol, and 6 parts of stir-baked squama manitis.

The processing method therefor includes the following steps in sequence:

preparation of materials: measuring raw materials of formula ratio according to composition of the Chinese herbal oral paste, and washing raw materials, except tortoise-plastron gelatin, turtle shell gelatin, donkey-hide gelatin, and xylitol, for subsequent use;

soaking: soaking the cleaned raw materials with 9 folds of water for 13 h, with the water over the raw materials by 17 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted tortoise-plastron gelatin, turtle shell gelatin, and donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Experiment Example 1

The following are a test of effects of the Chinese herbal oral paste for conditioning blood stasis constitution prepared according to Embodiment 5 of the present disclosure.

Basic conditions of cases: 120 clinical cases of blood stasis constitution, including 60 male cases and 60 female cases. The youngest was aged 6, and the oldest was aged 79. 20 cases had chest pain and cough, anhelation, could not lie on the back due to dyspnea, suffered from chest stuffiness, palpitation, had dark purple tongue possibly with ecchymoses or petechiae; 20 cases had palpitation, cyanotic lips, cyanotic tongue possibly with ecchymoses or petechiae, unsmooth pulse or with drop beat; 20 cases had stomachache, and stomachache got worse when the stomach was pressed, the pain was aggravated after eating or the stomach had masses, stomachache was aggravated at night, even with the syndromes of hematochezia or haematemesis; 20 cases had painful swelling or bruises locally on the body, had purple tongue possibly with ecchymoses or petechiae; 20 cases had pain in lower abdomen, irregular menstruation, dysmenorrhea, had purplish black menses with coagula, and had dark purple tongue possibly with ecchymoses; 20 cases suffered from vertigo, prolonged headache, accompanied with the syndromes of amnesia, insomnia, palpitation, tinnitus and deafness, and had dark purple tongue possibly with ecchymoses.

Usage and dosage: 25 g each time, once a day. Brew 25 g of the oral paste with boiling water in a cup, and stir them to make the oral paste melt for administration.

Evaluation criteria for therapeutic effects:

Cured: clinical symptoms were completely eliminated, and normal life was restored.

Effective: clinical symptoms were partially eliminated, and various signs were gradually improved.

Ineffective: symptoms and signs were not obviously improved.

Result statistics: 74 cases cured, effective to 31 cases, and ineffective to 15 cases, i.e., effective to 105 cases in total, therefore the total effective rate was 87.5%.

Experiment Example 2: Animal Experiment

An animal experiment is conducted on blood stasis model rats using the Chinese herbal oral paste prepared in Embodiments 1 to 5 to study the therapeutic effects of the Chinese herbal oral paste of the present disclosure on the experimental rats through control experiment.

(1) Hemorrheological Measurement:

The measurement method is as follows: after the rats were anesthetized, blood was drawn from the lower common carotids by means of catheterization, a multifunctional capillary viscometer was used to measure the whole blood viscosity $\eta b$ respectively at a high shear rate ($200 \text{ s}^{-1}$), a median shear rate ($30 \text{ s}^{-1}$) and a low shear rate ($5 \text{ s}^{-1}$), and an erythrocyte deformation & aggregation tester was used to measure the erythrocyte aggregation index RI.

(2) Creation of Acute Blood Stasis Rat Models

The SD rats in all the groups with the exception of the blank control group were administered with epinephrine Adr (0.8 mg/kg) by hypodermic injection, and then placed in an ice water bath for 4 minutes, 4 hours later, Adr was administered once again. 12 hours after the last injection, blood was drawn from the common carotids by means of catheterization, measurement was conducted to determine whether there is a significant difference between the model group and the blank control group in hemorrheological indexes $\eta b$ (high shear, median shear and low shear) and RI so as to determine whether the modeling was successful.

(3) Administration Mode

The blank control group (referred to as the blank group): saline (20 mL/kg) in a volume equal to that of the model group;

the acute blood stasis model group (referred to as the model group): saline (20 mL/kg); and the Chinese herbal oral paste experimental group (referred to as the experimental group): intragastrically administered with Chinese herbal oral paste at a dosage of 0.4 g/kg.

The experimental animals in each group were intragastrically administered twice a day, one in the morning and the other in the evening, for 5 days in total, and 5 days later, blood was drawn from the common carotids of the rats in each group by means of catheterization, and hemorrheological indexes $\eta b$ (high shear, median shear and low shear) and the erythrocyte aggregation index RI of each group were measured.

(4) Test Results and Data Analysis (See the Tesults in Table 1)

Compared with the blank group, both the whole blood viscosity (200, 30, $5 \text{ s}^{-1}$) and erythrocyte aggregation index of the model group were increased (P<0.01), which demonstrates that the acute blood stasis models is successful.

Compared with the model group, all of the Chinese herbal oral paste prepared in Embodiments 1-5 above could reduce the whole blood viscosity and the erythrocyte aggregation index of the model rats.

(5) Embodiment 5 is Superior to Embodiments 1-4 in Improving Hemorrheology-Related Indexes (ηb and RI).

Thus, taking the results into account comprehensively, the Chinese herbal oral paste prepared by the present disclosure can obviously improve hemorrheology, and can be used for the improvement and conditioning of the blood stasis constitution.

TABLE 1

Detection Results of Whole Blood Viscosity and Erythrocyte Aggregation Index of Acute Blood Stasis Rat Models

| Group | Hb (mPa · s) | | | RI |
|---|---|---|---|---|
| | $200\ s^{-1}$ | $30\ s^{-1}$ | $5\ s^{-1}$ | |
| Blank Group | 3.55 ± 0.47 | 5.30 ± 0.57 | 9.28 ± 0.73 | 3.25 ± 0.57 |
| Model Group | 4.64 ± 0.56** | 6.68 ± 0.79** | 12.20 ± 1.46* | 3.91 ± 0.68** |
| Embodiment 1 | 4.01 ± 0.38# | 6.42 ± 0.53## | 10.17 ± 0.97# | 3.66 ± 0.35# |
| Embodiment 2 | 4.15 ± 0.67## | 6.02 ± 0.64## | 9.99 ± 0.82## | 3.74 ± 0.44## |
| Embodiment 3 | 3.79 ± 0.52## | 5.48 ± 0.66# | 9.65 ± 0.65## | 3.47 ± 0.68## |
| Embodiment 4 | 3.80 ± 0.33## | 5.44 ± 0.83## | 9.54 ± 0.77## | 3.36 ± 0.39## |
| Embodiment 5 | 3.61 ± 0.81## | 5.27 ± 0.46## | 8.79 ± 0.69# | 3.22 ± 0.58## |

**$P < 0.01$ (compared with the blank group);
*$P < 0.05$ (compared with the blank group);
$P < 0.01$ (compared with the model group); and
$P < 0.05$ (compared with the model group)

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can be effective as sustained release, then a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning blood stasis constitution, comprising the following components in parts by weight: 5-19 parts of unprocessed rehmannia root, 6-17 parts of peony root, 6-15 parts of angelica, 3-14 parts of sichuan lovage rhizome, 7-18 parts of motherwort herb, 6-15 parts of peach seed, 2-10 parts of safflower, 1-5 parts of licorice, 6-15 parts of orange fruit, 4-13 parts of platycodon root, 4-13 parts of twotoothed achyranthes root, 5-17 parts of rose flower, 3-14 parts of cortex moutan, 10-27 parts of kudzu vine root, 3-9 parts of nutgrass galingale rhizome, 5-16 parts of unprocessed cattail pollen, 1-5 parts of Chinese cinnamon, 6-17 parts of earthworm, 13-30 parts of suberect spatholobus stem, 6-14 parts of largeleaf gentian root, 8-17 parts of milkvetch root, 8-17 parts of snakegourd root, 7-17 parts of danshen root, 6-16 parts of sanqi powder, 7-16 parts of India madder root, 12-31 parts of unprocessed hawthorn fruit, 5-15 parts of donkey-hide gelatin, 10-22 parts of turtle shell gelatin, 9-21 parts of tortoise-plastron gelatin, 20-40 parts of xylitol, and 3-9 parts of stir-baked squama manitis.

2. The Chinese herbal oral paste for conditioning blood stasis constitution of claim 1, wherein the unprocessed rehmannia root is 8-16 parts by weight, the peony root is 9-15 parts by weight, the angelica is 8-12 parts by weight, the sichuan lovage rhizome is 5-11 parts by weight, the motherwort herb is 9-15 parts by weight, the peach seed is 8-12 parts by weight, the safflower is 4-8 parts by weight, the licorice is 2-4 parts by weight, the orange fruit is 8-12 parts by weight, the platycodon root is 6-10 parts by weight, the twotoothed achyranthes root is 6-10 parts by weight, the rose flower is 9-14 parts by weight, the cortex moutan is 6-10 parts by weight, the kudzu vine root is 15-25 parts by weight, the nutgrass galingale rhizome is 5-7 parts by weight, the unprocessed cattail pollen is 8-13 parts by weight, the Chinese cinnamon is 1-3 parts by weight, the earthworm is 9-13 parts by weight, the suberect spatholobus stem is 15-25 parts by weight, the largeleaf gentian root is 8-12 parts by weight, the milkvetch root is 10-14 parts by weight, the snakegourd root is 10-14 parts by weight, the danshen root is 10-15 parts by weight, the sanqi powder is 8-13 parts by weight, the India madder root is 9-14 parts by weight, the unprocessed hawthorn fruit is 15-25 parts by weight, the donkey-hide gelatin is 8-13 parts by weight, the turtle shell gelatin is 12-18 parts by weight, the tortoise-plastron gelatin is 12-18 parts by weight, the xylitol is 25-35 parts by weight, and the stir-baked squama manitis is 5-7 parts by weight.

3. The Chinese herbal oral paste for conditioning blood stasis constitution of claim 1, wherein the unprocessed rehmannia root is 12 parts by weight, the peony root is 12 parts by weight, the angelica is 10 parts by weight, the sichuan lovage rhizome is 8 parts by weight, the motherwort herb is 12 parts by weight, the peach seed is 10 parts by weight, the safflower is 6 parts by weight, the licorice is 3 parts by weight, the orange fruit is 10 parts by weight, the platycodon root is 8 parts by weight, the twotoothed achyranthes root is 8 parts by weight, the rose flower is 12 parts by weight, the cortex moutan is 8 parts by weight, the kudzu vine root is 20 parts by weight, the nutgrass galingale rhizome is 6 parts by weight, the unprocessed cattail pollen is 10 parts by weight, the Chinese cinnamon is 2 parts by weight, the earthworm is 10 parts by weight, the suberect spatholobus stem is 20 parts by weight, the largeleaf gentian root is 10 parts by weight, the milkvetch root is 12 parts by weight, the snakegourd root is 12 parts by weight, the danshen root is 12 parts by weight, the sanqi powder is 10 parts by weight, the India madder root is 12 parts by weight, the unprocessed hawthorn fruit is 20 parts by weight, the donkey-hide gelatin is 10 parts by weight, the turtle shell gelatin is 15 parts by weight, the tortoise-plastron gelatin is 15 parts by weight, the xylitol is 30 parts by weight, and the stir-baked squama manitis is 6 parts by weight.

4. A processing method for the Chinese herbal oral paste for conditioning blood stasis constitution of claim 1, comprising the following steps in sequence: preparation of materials, soaking, decoction, concentration, and collecting an oral paste.

5. The processing method for the Chinese herbal oral paste for conditioning blood stasis constitution of claim 4, wherein the step of preparation of materials is: measuring raw materials of formula ratio according to composition of the Chinese herbal oral paste, and washing raw materials, except tortoise-plastron gelatin, turtle shell gelatin, donkey-hide gelatin, and xylitol, for subsequent use.

6. The processing method for the Chinese herbal oral paste for conditioning blood stasis constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning blood stasis constitution of claim 6, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use.

8. The processing method for the Chinese herbal oral paste for conditioning blood stasis constitution of claim 7, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

9. The processing method for the Chinese herbal oral paste for conditioning blood stasis constitution of claim 8, wherein the step of collecting an oral paste is: pouring xylitol, and melted tortoise-plastron gelatin, turtle shell gelatin, and donkey-hide gelatin into the vegetarian paste respectively, stirring them continuously with a shovel while cooking them slowly with low heat, until the juice can coagulate into beads when being dropped into clear water and does not disperse, then canning the resulted oral paste.

10. The processing method for the Chinese herbal oral paste for conditioning blood stasis constitution of claim 9, wherein the melting step is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

11. A processing method for the Chinese herbal oral paste for conditioning blood stasis constitution of claim 2, comprising the following steps in sequence: preparation of materials, soaking, decoction, concentration, and collecting an oral paste.

12. The processing method for the Chinese herbal oral paste for conditioning blood stasis constitution of claim 11, wherein the step of preparation of materials is: measuring raw materials of formula ratio according to composition of the Chinese herbal oral paste, and washing raw materials, except tortoise-plastron gelatin, turtle shell gelatin, donkey-hide gelatin, and xylitol, for subsequent use.

13. The processing method for the Chinese herbal oral paste for conditioning blood stasis constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning blood stasis constitution of claim 13, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use.

15. The processing method for the Chinese herbal oral paste for conditioning blood stasis constitution of claim 14, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

16. The processing method for the Chinese herbal oral paste for conditioning blood stasis constitution of claim 15, wherein the step of collecting an oral paste is: pouring xylitol, and melted tortoise-plastron gelatin, turtle shell gelatin, and donkey-hide gelatin into the vegetarian paste respectively, stirring them continuously with a shovel while cooking them slowly with low heat, until the juice can coagulate into beads when being dropped into clear water and does not disperse, then canning the resulted oral paste.

17. The processing method for the Chinese herbal oral paste for conditioning blood stasis constitution of claim 16, wherein the melting step is: smashing lumps of tortoise-plastron gelatin, turtle shell gelatin, and donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

18. A processing method for the Chinese herbal oral paste for conditioning blood stasis constitution of claim 3, comprising the following steps in sequence: preparation of materials, soaking, decoction, concentration, and collecting an oral paste.

19. The processing method for the Chinese herbal oral paste for conditioning blood stasis constitution of claim 18, wherein the step of preparation of materials is: measuring raw materials of formula ratio according to composition of the Chinese herbal oral paste, and washing raw materials, except tortoise-plastron gelatin, turtle shell gelatin, donkey-hide gelatin, and xylitol, for subsequent use.

20. The processing method for the Chinese herbal oral paste for conditioning blood stasis constitution of claim 19, wherein the soaking step is: soaking the cleaned raw materials with 8-10 folds of water for 8-15 h, with the water over the raw materials by 10-20 cm.

* * * * *